(12) United States Patent
Inman et al.

(10) Patent No.: US 6,899,104 B1
(45) Date of Patent: May 31, 2005

(54) WOUND CLOSURE DEVICE FOR VIEWING A WOUND AND METHOD

(75) Inventors: J. D. Inman, Santa Barbara, CA (US); Cubie E Ward, Jr., Grand Prairie Tarvant, TX (US); Tod H. Schultz, Arlington, TX (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/400,059

(22) Filed: Sep. 21, 1999

Related U.S. Application Data (63) Continuation of application No. 08/858,015, filed on May 16, 1997, now Pat. No. 5,960,795, which is a continuation-in-part of application No. 08/544,146, filed on Oct. 17, 1995, now Pat. No. 5,630,430, which is a continuation-in-part of application No. 08/278,575, filed on Jul. 20, 1994, now Pat. No. 5,497,788, which is a continuation of application No. 08/092,594, filed on Jul. 16, 1993, now abandoned.

(51) Int. Cl.[7] ............................................. A61F 13/00
(52) U.S. Cl. ...................................... 128/888; 602/43
(58) Field of Search ................................ 128/888, 889; 602/41–43, 47, 52, 57

(56) References Cited

U.S. PATENT DOCUMENTS

| | | |
|---|---|---|
| 1,644,508 A | 10/1927 | Blake |
| 3,645,835 A | 2/1972 | Hodgson |
| 3,918,446 A | 11/1975 | Buttaravoli |
| 4,096,863 A | 6/1978 | Kaplan et al. |
| 4,165,748 A | 8/1979 | Johnson |
| 4,275,721 A | 6/1981 | Olson |
| 4,450,845 A | 5/1984 | Engel |
| 4,583,976 A | 4/1986 | Ferguson |
| 4,598,004 A | 7/1986 | Heinecke |
| 4,600,001 A | 7/1986 | Gilman |
| 4,614,183 A | 9/1986 | McCracken et al. |
| 4,641,643 A | * 2/1987 | Greer .......................... 128/888 |
| 4,669,458 A | 6/1987 | Abraham et al. |
| 4,678,462 A | 7/1987 | Vaillancourt |
| 4,704,177 A | 11/1987 | Vaillancourt |
| 4,730,611 A | 3/1988 | Lamb |
| 4,753,232 A | 6/1988 | Ward |

(Continued)

OTHER PUBLICATIONS

"Steri–Strip™ Wound Closure System" Surgical Division, 3M Healthcare, ©1992 3M (3 Pages).
"Alexander's Care of the Patient in Surgery" M. Mosby, ©1995 Mosby–Year Book, Inc. (4 Pages).

Primary Examiner—Michael A. Brown
(74) Attorney, Agent, or Firm—Dority & Manning, P.A.

(57) ABSTRACT

A unitary wound closure device adapted to permit a wound on a patient to be viewed while the closure device is secured to the patient. The device comprises a body having sufficient flexibility for it to be folded against itself. The body includes first and second surfaces facing away from one another, a securing portion having a length and width sufficient to secure facing edges of the wound in close juxtaposition with one another and viewing portion having a length and width sufficient to circumscribe the wound of the patient. A first quantity of adhesive-substance is disposed on the first surface of the body to adhere the securing portion of the body to the patient. A second quantity of adhesive substance is disposed on the second surface of the body to adhere the viewing portion to the patient and the securing portion when the viewing portion is folded over and onto the protecting portion and the patient. The wound closure device may also include a hinge member joining the securing portion and the viewing portion.

13 Claims, 8 Drawing Sheets

U.S. PATENT DOCUMENTS

| | | |
|---|---|---|
| 4,815,457 A | 3/1989 | Mazars et al. |
| 4,838,868 A | 6/1989 | Forgar et al. |
| 4,875,896 A | 10/1989 | Kurtz |
| 4,898,587 A | 2/1990 | Mera |
| 4,907,599 A | 3/1990 | Taylor |
| 4,926,850 A | 5/1990 | Lott et al. |
| 5,000,172 A | 3/1991 | Ward |
| 5,012,801 A | 5/1991 | Feret |
| 5,018,516 A | 5/1991 | Gilman |
| 5,025,783 A | 6/1991 | Lamb |
| 5,092,323 A | 3/1992 | Riedel et al. |
| 5,116,324 A | 5/1992 | Brierley et al. |
| 5,127,423 A | 7/1992 | Draeger |
| 5,160,328 A | 11/1992 | Cartmell |
| 5,170,781 A | 12/1992 | Loomis |
| 5,181,914 A | 1/1993 | Zook |
| 5,183,664 A | 2/1993 | Ansell |
| 5,197,493 A | 3/1993 | Grier-Idris |
| 5,254,338 A | 10/1993 | Sakai et al. |
| 5,263,970 A | 11/1993 | Preller |
| 5,282,791 A | 2/1994 | Lipton et al. |
| 5,306,504 A | 4/1994 | Lorenz |
| 5,336,162 A | 8/1994 | Ota |
| 5,336,219 A | 8/1994 | Krantz |
| 5,415,627 A | 5/1995 | Rasmussen et al. |
| 5,497,788 A * | 3/1996 | Inman .................. 602/43 |
| 5,520,629 A | 5/1996 | Heinecke et al. |
| D385,038 S | 10/1997 | Shultz |

* cited by examiner

WOUND CLOSURE DEVICE FOR VIEWING A WOUND AND METHOD

RELATED APPLICATIONS

This application is a continuation of application Ser. No. 08/858,015, filed May 16, 1997, now U.S. Pat. No. 5,960,795, which is a continuation-in-part of application Ser. No. 08/544,146, filed Oct. 17, 1995, now U.S. Pat. No. 5,630,430 dated May 20, 1997, which is a continuation-in-part of application Ser. No. 08/278,575, filed Jul. 20, 1994, now U.S. Pat. No. 5,497,788 dated Mar. 12, 1996, which is a continuation of application Ser. No. 08/092,594 filed Jul. 16, 1993, now abandoned.

TECHNICAL FIELD OF THE INVENTION

This invention relates generally to devices for covering wounds, lacerations, incisions, inserted medical devices and the like. More particularly, but not by way of limitation, this invention relates to an improved device having one or more adhesive layers for covering wounds, lacerations, incisions, and inserted medical devices that can be easily applied by a person wearing surgical gloves and the like.

BACKGROUND OF THE INVENTION

The use of film dressing is well known for the purpose of covering wounds. Usually, such wounds are relatively small or are located in a position where there is little or no distension of the skin as a result of movement by the injured person. Wounds, incisions, lacerations, insertion of medical devices, and any related skin traumas wherein there is a separation or penetration of a patient's skin are interchangeable terms as used herein.

An example of a transparent film dressing is given by Robert W. McCracken, et al., in U.S. Pat. No. 4,614,183, issued Sep. 30, 1986. The device is often difficult to apply when the user is wearing surgical gloves.

Another example of a transparent film dressing, which also includes a wound closure feature is embodied in a device sold under the trade name "Steri-Strip", Laparoscopic Wound Closure System featuring "Tegaderm" Transparent Dressing and made by the Medical-Surgical Division of 3M Health Care, and related to U.S. Pat. No. 3,645,835. When using this dressing, it appears that a narrow closure member is removed, or partially removed, from a release treated paper backing and applied to close the wound. It is then necessary to remove a very thin transparent film that is separate from the closure member and apply this film to cover the area of the trauma. While this device may effectively cover the wound, it is often difficult to apply when wearing gloves.

SUMMARY OF THE INVENTION

In accordance with teachings of the present invention, an improved wound covering device is provided to substantially reduce or eliminate shortcomings previously associated with such wound covering devices.

The terms "viewing portion" and "cover dressing" are used interchangeably, and the terms "securing portion" and "handle member" are used interchangeably throughout this specification.

According to one aspect of the present invention a wound covering device for covering and sealing at least a portion of a patient's wound includes an elongated handle member and a cover dressing which is releasably secured to the handle member by a first adhesive layer. The first adhesive layer may be used to secure the cover dressing to an area of skin adjacent to a patient's wound when the cover dressing is disposed in an overlying relation to the wound. The wound covering device further including a flexible hinge member having a width that is approximately coextensive with a portion of the wound to be covered. The flexible hinge member further having a first portion disposed on the cover dressing and a second portion disposed on the handle member. The first portion of the flexible hinge member preferably affixed to the cover dressing by a second adhesive layer. The wound covering device still further including a third adhesive layer disposed on a side of the flexible hinge member remote from the cover dressing for securing the flexible hinge member to the patient's skin adjacent to the wound.

According to another aspect of the present invention, a wound covering device may include a transparent portion in the handle member for facilitating alignment of the wound covering device relative to at least a portion of the wound to be covered.

According to yet another aspect of the present invention, a wound covering device includes a primary dressing disposed on the second portion of the hinge member.

BRIEF DESCRIPTION OF THE DRAWINGS

For a more complete understanding of the present invention, and the advantages thereof, reference is now made to the following written description taken in conjunction with the accompanying drawings in which like reference numbers indicate like features, and wherein.

DETAILED DESCRIPTION OF THE INVENTION

The preferred embodiments of the present invention and its advantages are best understood by referring to FIGS. 1–40 of the drawings, like numerals being used for like and corresponding parts of the various drawings. It will be understood that the thicknesses of the layers of materials and other dimensions in the drawings have been greatly exaggerated for purposes of illustration.

Figure 1A:
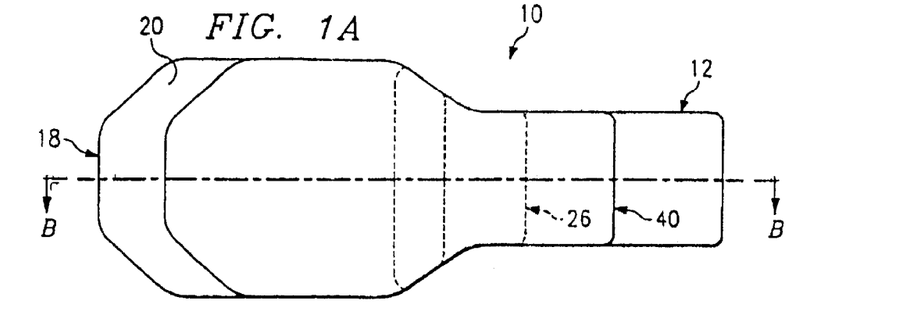
FIG. 1A is a top view of a wound covering device constructed in accordance with teachings of the present invention.
Figure 1B:
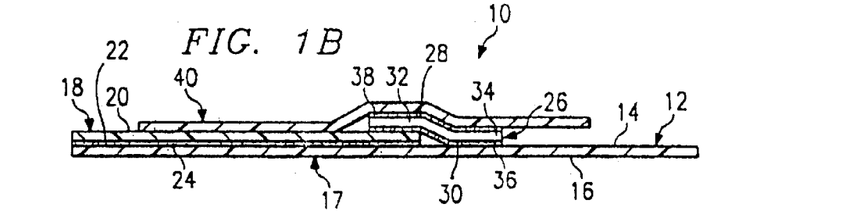
FIG. 1B is a sectional view of the wound covering device of FIG. 1A taken generally along line B—B of FIG. 1A.
Figure 1C:
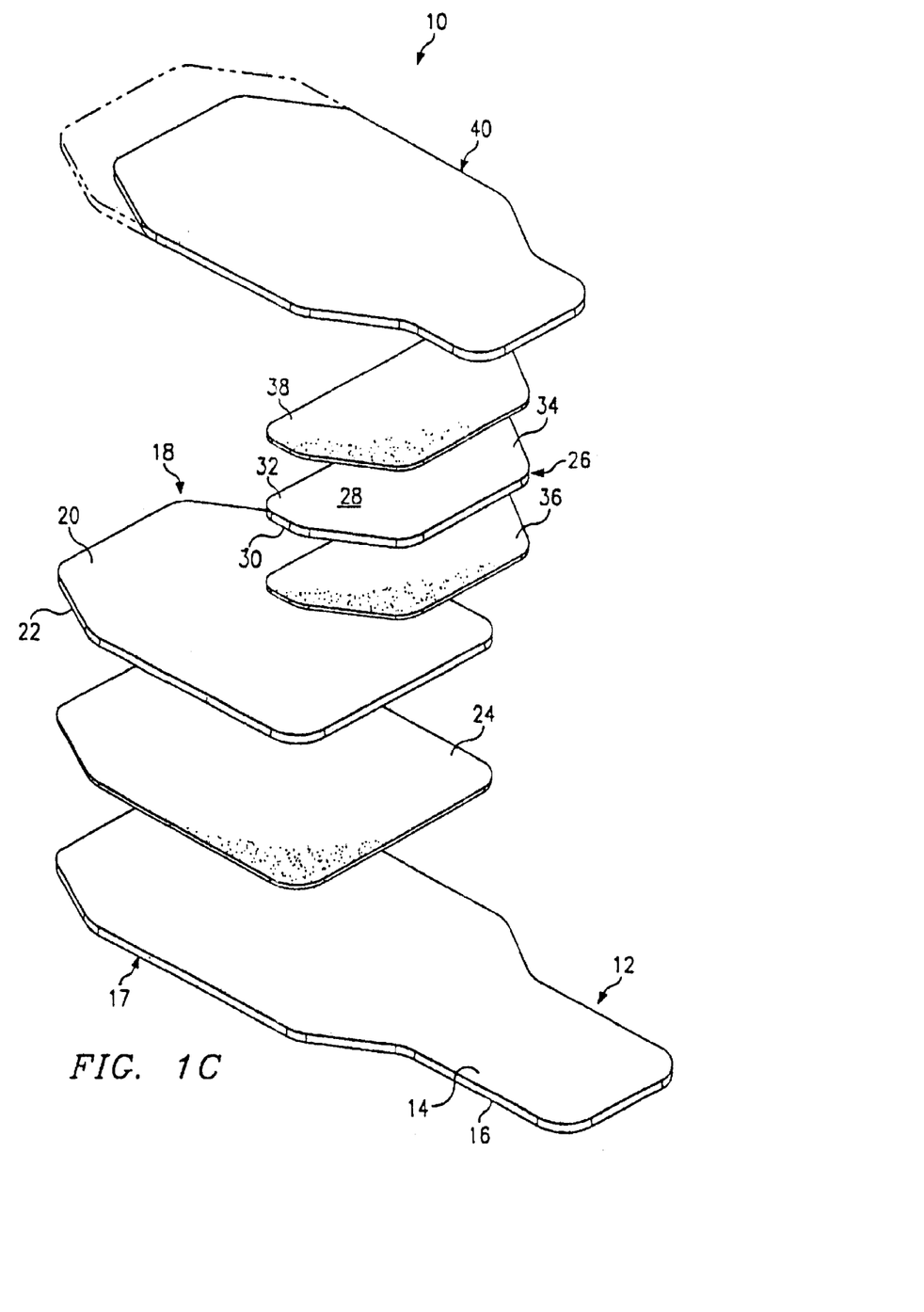
FIG. 1C is an exploded view of the wound closure device of FIG. 1A.

FIGS. 1A–1C show various views of a wound covering device 10. Wound covering device 10 includes elongated handle member 12, which has first side 14 and second side 16. Wound covering device 10 further includes cover dressing 18 having first side 20 and second side 22. First adhesive layer 24 may be disposed on first side 22 of cover dressing 18 such that adhesive layer 24 resides between first side 22 of cover dressing 18 and first side 14 of handle member 12. Wound covering device 10 may also include flexible hinge member 26 having first side 28 and second side 30. Hinge member 26 preferably has a width that is approximately coextensive with a portion of the wound to be covered by wound covering device 10. Hinge member 26 may further include first portion 32 and second portion 34. Second adhesive layer 36 may be disposed on second side 30 of flexible hinge member 26. For the embodiment shown in FIGS. 1B and 1C, second adhesive layer 36 extends over second side 30 of first portion 32 and second portion 34. For some applications, second adhesive layer 36 may only be disposed on second side 30 corresponding with first portion 32.

Third adhesive layer 38 may further be disposed on first side 28 of hinge member 26. First portion 32 of hinge member 26 is disposed on cover dressing 18 such that second adhesive layer 36 resides between cover dressing 18 and hinge member 26. Second portion 34 of hinge member 26 is disposed on first side 14 of handle member 12. Second adhesive layer 36 may or may not reside between first portion 32 of hinge member 26 and side 14 of handle member 12. Protective member 40 may be disposed on third adhesive layer 38. Protective member 40 may extend beyond first portion 32 of hinge member 26 to cover some or all of first side 20 of cover dressing 18. Similarly, protective member 40 may extend beyond second portion 34 of hinge member 26 to cover some or all of first side 14 of handle member 12.

Handle member 12 preferably includes an enlarged portion 17 that is at least coextensive with cover dressing 18 so as to prevent undesired exposure of first adhesive layer 24. Provided a portion of handle member 12 is at least coextensive with first adhesive layer 24, handle member 12 may take any size and shape appropriate for a particular application. Handle member 12 may be transparent or opaque, and may be formed from a variety of materials, such as paper, polyester, polyethylene or laminates of these materials. In addition, handle member 12 may be silicon coated on first side 14 to facilitate easy release from cover dressing 18.

First adhesive layer 24 operates to adhere second side 22 of cover dressing 18 to a patient's skin surrounding a wound. To accomplish this objective, first adhesive layer 24 may, but need not be coextensive with second side 22 of cover dressing 18. First adhesive layer 24 may occupy any area of cover dressing 18 suitable to create an adequate bond between cover dressing 18 and the skin surrounding the wound. For example, first adhesive layer 24 may be located in a relatively narrow band around the periphery of cover dressing 18. To assist in the healing process, adhesive layer 24 may be impregnated with a variety of medicinal agents, such as antimicrobial compounds, antifungal compounds and/or antibacterial compounds. First adhesive layer 24 further operates to releasably attach first side of handle member 12 to second side 22 of cover dressing 18. A release coating may be applied to first side 14 of handle member 12 so that handle member 12 can be readily separated from cover dressing 18 despite the presence of adhesive layer 24.

Cover dressing 18 operates to cover at least a portion of the wound to be covered. Where cover dressing 18 is coextensive with or larger than the wound to be covered, cover dressing may be used to cover the entire wound. In cases where cover dressing 18 is smaller than the area to be covered, multiple wound covering devices may be used to cover the entire wound. Cover dressing 18 may be fashioned in any shape, size and configuration appropriate to specific applications.

When disposed in an overlying relation to the wound, cover dressing 18 preferably forms a barrier around the portion of the wound covered. This barrier may prevent external contaminants from entering the wound site, and may also prevent wound exudates from leaking from the wound site. Cover dressing 18 may be transparent or opaque. Utilizing a transparent cover dressing is advantageous in that is facilitates observation of the wound throughout the healing process. Cover dressing 18 may be formed form a variety of materials, such as polyethylene, polyurethane, polypropylene, polyester, woven or nonwoven substrates or hydrogel. Depending on the application, cover dressing 18 may comprise a hydrophobic material or a hydrophilic material. To further assist the healing process, cover dressing 18 may be loaded with one or more medicinal agents, such as antimicrobial compounds, antifungal compounds, and/or antibiotic compounds.

Hinge member 26 operates to secure wound covering device 10 to a selected location or locations adjacent to a patient's wound. Hinge member 26 preferably has a width that is approximately coextensive with the portion of the wound to be covered by a cover dressing 18. It should be noted that hinge member 26 need not be exactly coextensive with the portion of the wound to be covered. Hinge member 26 may be somewhat smaller or larger than the portion of the wound to be covered without departing from the spirit of the invention. In addition, hinge member 26 may be any length. In some applications a primary dressing (not shown) may be affixed to hinge member 26 and subsequently aligned over a portion of the wound to be covered. Details of affixing and utilizing a primary dressing are described below. Hinge member 26 may be transparent or opaque and may be formed from a variety of materials including polyethylene, polyurethane, polyester, woven substrates, non-woven substrates, hydrogel or foam. To further assist in the healing process, hinge member 26 may be loaded with one or more medicinal agents, such as antimicrobial compounds, antifungal compounds, and/or an antibiotic compound. Details of the function of hinge member 26 are described below.

Second adhesive layer 36 serves to connect first side 20 of cover dressing 18 with second side 30 of first portion 32 of hinge member 26. Second adhesive layer 36 may be disposed on first side 20 of cover dressing 18, or on second side 30 of first portion 32 of hinge member 26. Second adhesive layer 36 may occupy any portion of first side 20 of cover dressing 18 or second side 30 of first portion 32 of hinge member 26 suitable to create a bond between the two structures. Second adhesive layer 36 may, but need not reside between handle member 12 and second side 30 of second portion 34 of hinge member 26.

Third adhesive layer 38 may cover both first portion 32 and second portion 34 of first side 28 of hinge member 26. Third adhesive layer 38 serves to bond first side 28 of hinge member 26 to a selected area of skin adjacent to a patient's wound. Third adhesive layer 38 may occupy any area of first side 28 of hinge member 26 suitable to create an effective bond between first side 28 of hinge member 26 and the selected area of the patient's skin adjacent to a wound. To assist in the healing process, third adhesive layer 38 may be impregnated with a variety of medicinal agents, such as antimicrobial compounds, antifungal compounds and/or antibacterial compounds.

It should be observed that when then caregiver peels handle member 12 away from second portion 34 of hinge member 26, any adhesive residing between handle member 12 and second portion 34 of hinge member 26 may tend cause hinge member 26 to be peeled away from the patient's skin. To ensure that hinge member 26 is not removed from the patient's skin when handle member 12 is peeled away, it may be advantageous to leave part of second side 30 of second portion 34 of hinge member 26 free from adhesive. For example, an area of second side 30 of second portion 34 of hinge member 26 remote from cover dressing 18 may be left free from second adhesive layer 36. In this way, third adhesive layer 38 may form a primary bond between hinge member 26 and the patient's skin, while second adhesive layer 36 forms a weaker secondary bond between handle member 12 and second portion 34 of hinge member 26. The caregiver may then peel handle member 12 away from second portion 34 of hinge member 26 without removing hinge member 26 from the patient's skin adjacent to the wound.

Protective member 40 is preferably releasably attached to hinge member 26 by third adhesive layer 38. A release coating may be applied to the side of protective member 40 adjacent to third adhesive layer 38 sot that protective member 40 can be easily separated from hinge member 26 despite the presence of third adhesive layer 38. Protective member 40 is at least coextensive with third adhesive layer 38 so as to prevent undesired exposure of third adhesive layer 38 prior to its application to a patient's skin. Provided that protective member 40 is at least coextensive with third adhesive layer 38, it may take any size and shape. Protective layer 40 may be advantageously fashioned to have dimensions different from those of handle member 12 so that protective member 40 can be readily removed from hinge member 26 when wound covering device 10 is to be applied to the patient's skin adjacent to the wound. Protective member 40 may be formed from a variety of materials, such as paper, polyester, polyethylene, or laminates of these materials.

Figure 2A:
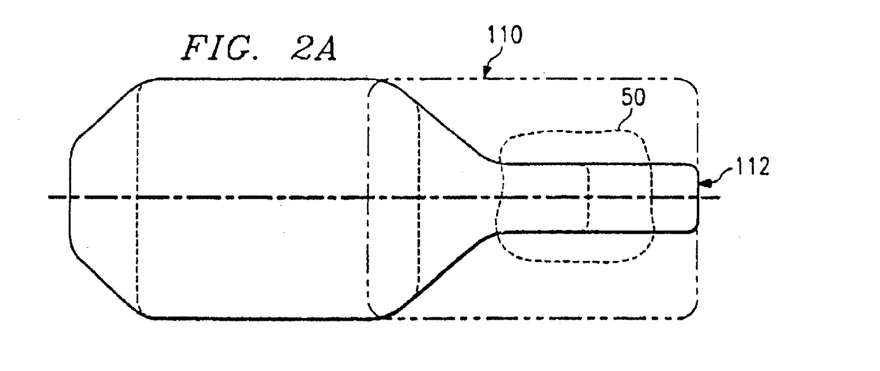
FIG. 2A is a top view of a wound covering device showing the associated handle member disposed over a wound.
Figure 2B:
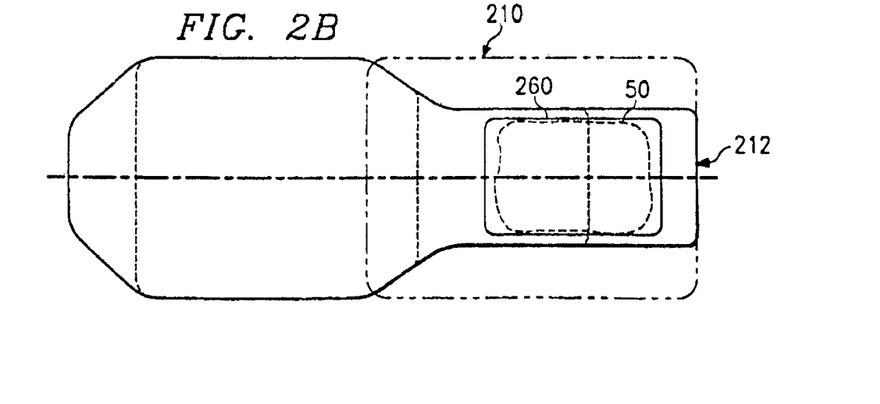
FIG. 2B is a top view of another embodiment of a wound covering device showing the associated handle member disposed over a wound.
Figure 2C:
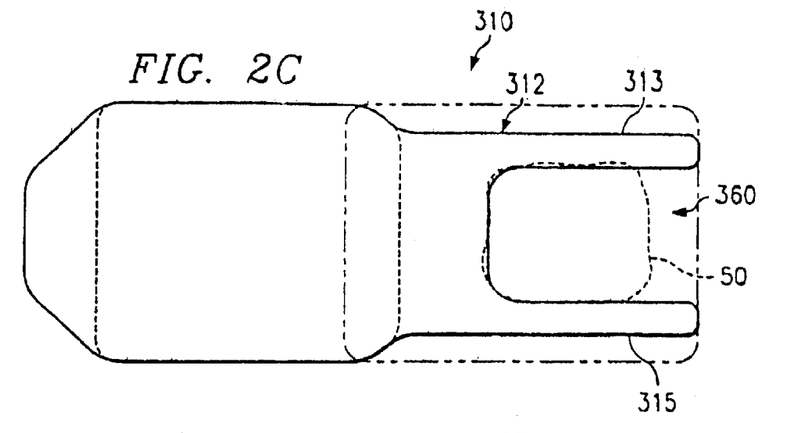
FIG. 2C is a top view of yet another embodiment of a wound covering device showing the associated handle member disposed over a wound.

FIGS. 2A–2C illustrate various embodiments of wound covering devices 110, 210 and 310, respectively, as well as a method of aligning the wound covering device over a wound according to teachings of the present invention. FIGS. 2A–2C illustrate that elongated handle members 112, 212 and 312 may take a variety of shapes and sizes. In one embodiment (FIG. 2A) handle member 112 may cover an area smaller than a portion of wound 50 to be covered. In such a case, a care giver may align wound covering device 110 by placing handle member 112 in a position approximately over the center of the portion of wound 50 to be covered. In another embodiment (FIG. 2B) handle member 212 may include viewing portion 260. Viewing portion 260 may comprise any portion, or all of handle member 212. In one embodiment, viewing portion 260 includes the entirety of handle member 212, which may be formed from a substantially transparent material to facilitate observation of wound 50 during alignment of wound covering device 210. In another embodiment, viewing portion 260 may comprise only a part of handle member 212. In such a case, viewing portion 260 may comprise a substantially transparent portion of an otherwise opaque handle member. In still another embodiment, viewing portion 260 may consist of an excised portion of handle member 212 through which all or part of wound 50 is visible. Handle member 212 may be die cut to any shape to form viewing portion 260.

FIG. 2C illustrates still another embodiment in which handle member 312 includes viewing portion 360 which has been die cut to suit a particular application. In this case, handle member 312 may include a first prong 313 and a second prong 315. Prongs 313 and 315 may be die cut to any size, shape or configuration suitable to a particular application. The configuration of handle member 312 may be useful in applications such as where a large dressing requires two hands to deliver the dressing to the wound site.

Figure 3:
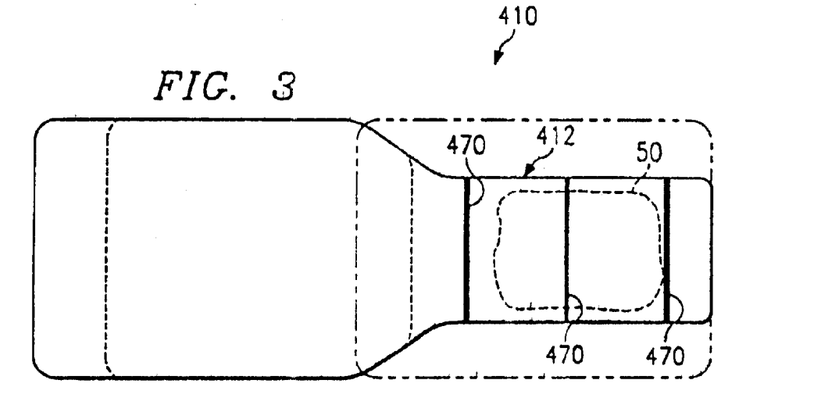
FIG. 3 is a top view of a wound covering device showing the associated handle member having an alignment pattern.

FIG. 3 illustrates a wound covering device 410 in which elongated handle member 412 includes alignment pattern 470 for aiding in placement of wound covering device 410 over wound 50. Although alignment pattern 470 is shown as three parallel lines, it should be noted that alignment pattern 470 could be any desired pattern helpful in aiding the care giver to align wound covering device 410 over wound 50. For example, alignment pattern 470 may be a single line, several offset lines, a centering point or a grid pattern. In addition to aiding the care giver in positioning wound covering device 410 over wound 50, alignment pattern 470 may be used to align wound covering device 410 over a medical device, such as a catheter or intravenous tube extending from the patient's skin.

FIGS. 4A–4D illustrate a method of applying a wound covering device 10 according to the teachings of the present invention. A caregiver 5 begins the method of applying wound covering device 10 by removing wound covering device 10 from a sterile package (not shown). Upon removing wound covering device from its packaging, there is no live adhesive exposed. Caregiver 5 proceeds by grasping handle member 12 and cover dressing 18, and removing protective member 40 to expose adhesive layer 38. Because there is no adhesive on the side 16 of handle member 12 or side 20 of cover dressing 18, caregiver 5 may grasp wound covering device 10 without sticking to it. Caregiver 5 may dispose of protective member 40 adjacent 38 removed before application to skin in 4B (as in 1B), or alternatively, may sketch or write notes on protective member 40 and retain it for future reference.

Figure 4A:
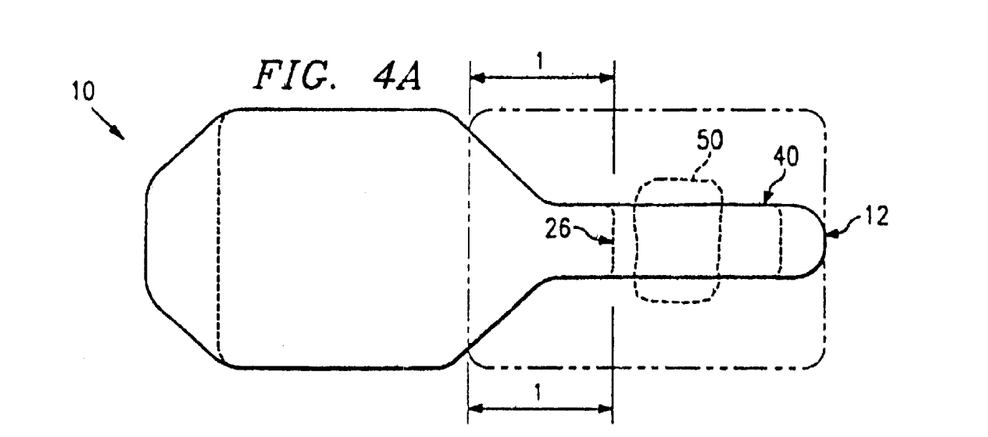
FIGS. 4A–4D are schematic drawings showing an exemplary method of applying a wound covering device according to teachings of the present invention.

Caregiver 5 may next align handle member 12 over a wound 50 to be covered (FIG. 4A). Caregiver 5 may be aided in aligning the handle member by viewing portion 260 or 360 and/or alignment pattern 470 (FIGS. 2B, 2C, and 3). If the wound covering device is used to cover and/or secure a medical device extending from a patient's skin, the caregiver will begin by aligning the medical device with an alignment pattern on the handle member. In that type of application, the present invention provides an advantage of enabling the caregiver to apply the wound covering device with one hand while holding the medical device secure with the other.

Figure 4B:
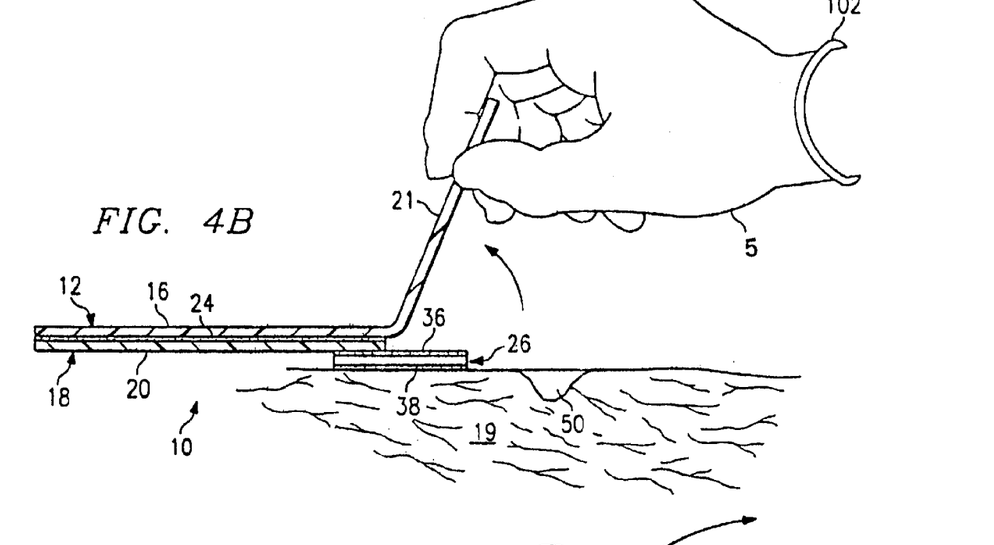
Figures 4C, 4D:
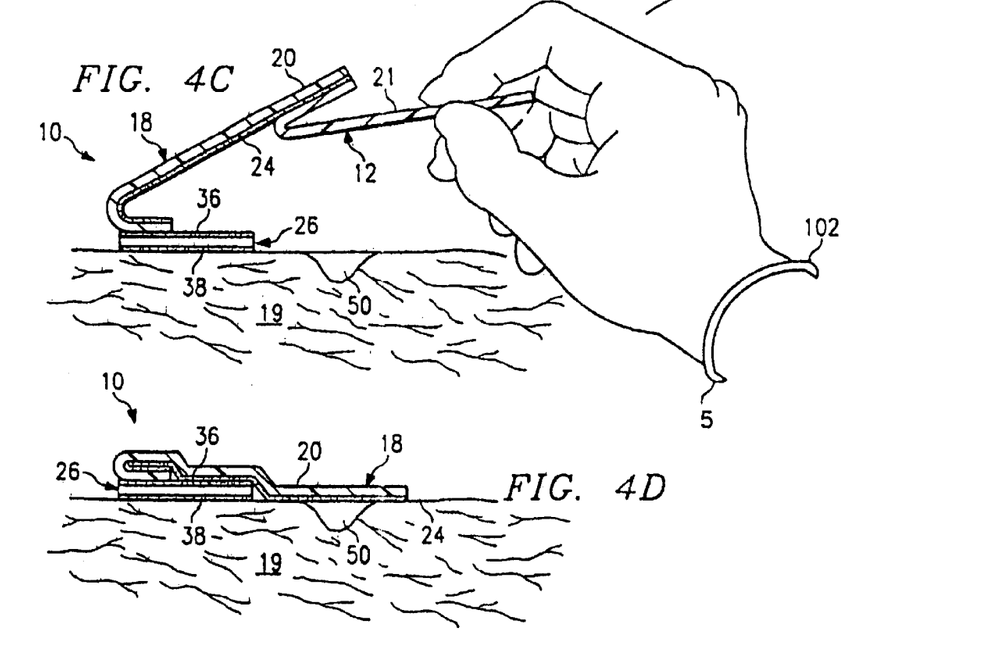

Once wound covering device 10 is properly aligned, caregiver 5 may apply pressure across area 1—1 to affix hinge member 26 to a patient's skin 19 adjacent to the portion of the wound to be covered. This causes wound covering device 10 to be affixed to the patient's skin in a location selected by caregiver 5. Caregiver 5 may next grasp handle member 12 at an area 21 remote from cover member 18, and peel handle member 12 away from hinge member 26 until cover dressing 18 is encountered (FIG. 4B). Upon encountering cover dressing 18, caregiver 5 peels handle member 12 away from cover dressing 18, drawing cover dressing over wound 50 (FIG. 4C). Caregiver 5 continues to peel handle member 12 from cover dressing 18 until cover dressing 18 overlies the wound and handle member 12 separates from cover dressing 18. Once handle member 12 has separated from cover dressing 18, caregiver 5 may write notes, such as the date of the application of wound covering device 10, on handle member 12, and retain handle member 12 in the patient's records for future reference. Additionally, caregiver 5 may sketch the outline of wound 50 on handle member 12 to make a record of the extent of the wound for future reference.

Once cover dressing 18 is disposed in an overlying relationship to wound 50, caregiver 5 may apply pressure to cover member 18 to affix it securely to the skin surrounding wound 50 (FIG. 4D). Cover member 18 forms a barrier around wound 50. This barrier may prevent external contaminants from entering the wound site, and may also prevent wound exudates from leaking from the wound site. In the case of application of wound covering device 10 to a medical device extending from the patient's skin, cover dressing 18 secures the position of the medical device and forms a similar barrier around the medical device.

Figure 5A:
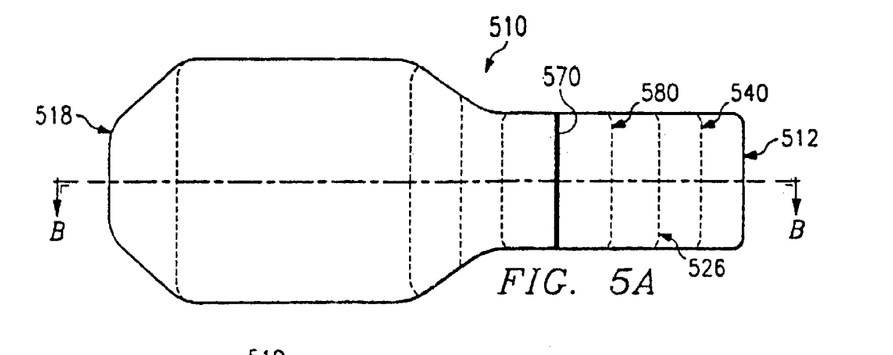
FIG. 5A is a top view of another embodiment of a wound covering device according to the teachings of the present invention.
Figure 5B:
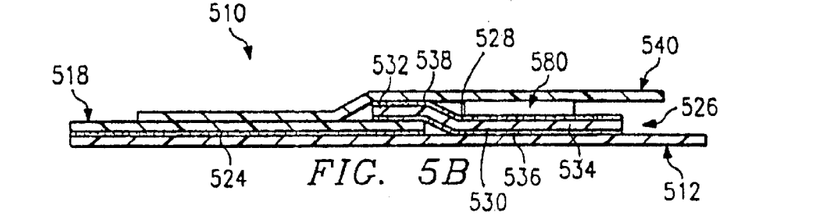
FIG. 5B is a drawing in section of the wound covering device shown in FIG. 5A taken generally along the line B—B.

FIGS. 5A and 5B show a top view and a cross-sectional view, respectively, of another embodiment of a wound covering device according to the teachings of the present invention. Wound covering device 510 is structurally similar to wound covering device 10 shown in FIGS. 1A–1C. Wound covering device 510 includes handle member 512, which is similar in structure and function to handle member 12 of FIGS. 1A–1C. Like handle member 412 shown in FIG. 3, handle member 512 may include an alignment pattern 570 for aiding in the alignment of wound covering device 510 over a wound. Alignment pattern 570 may be a variety of patterns, such as a single line, a set of parallel lines, a centering point or a grid pattern. Wound covering device 510 further includes a cover dressing 518 disposed on handle member 512. Cover dressing 518 is similar in structure and function to cover dressing 18 of FIGS. 1A–1C. A first adhesive layer 524, which is disposed on cover dressing 518, is similar in structure and function to adhesive layer 24 in FIGS. 1A–1C.

Wound covering device 510 further includes a flexible hinge member 526 having a first side 528 and a second side 530. Hinge member may further include a first portion 532 and a second portion 534. First portion 532 of hinge member 526 is disposed on cover dressing 518. A second adhesive layer 536 may reside between first portion 532 of hinge member 526 and cover dressing 518. Adhesive layer 536 may be disposed on cover dressing 18 or second side 530 of first portion 532 of hinge member 526. Adhesive layer 536 may occupy any portion of cover dressing 518 or first portion 532 of hinge member 56 suitable to create a bond between the two structures. Second portion 534 of hinge member 526 may be disposed on handle member 512. Adhesive layer 536 may or may not reside between handle member 512 and second portion 534 of hinge member 526. As previously described in reference to wound covering device 10, it may be advantageous to leave a part of second portion 534 of hinge member 526 free from second adhesive layer 536, thus avoiding separation of hinge member 526 from the patient's skin when handle member 512 is removed. First portion 532 of hinge member 526 is similar in structure and function to first portion 32 of hinge member 26 in FIGS. 1A–1C. Second portion 534 of hinge member 526 may be elongated to support a primary dressing 580 disposed on first side 528 of second portion 534 of hinge member 526. Wound covering device 510 may include primary dressing 580. If wound covering device 510 does not already include primary dressing 580, a caregiver may affix a primary dressing to hinge member 526.

A third adhesive layer 538 is disposed on at least a portion of hinge member 526 on first side 28 of hinge member 526 remote from handle member 512. Adhesive layer 538 serves to bond the side of hinge member 526 remote from handle member 52 to an area of skin adjacent to patient's wound. Adhesive layer 538 may occupy any area of the side of hinge member 526 remote from handle member 512 suitable to create an effective bond between hinge member 526 and an area of the patient's skin adjacent to a wound. Adhesive layer 538 may further function to adhere primary dressing 580 to first side 528 of second portion 534 of hinge member 526. Alternatively, primary dressing 580 may include its own adhesive layer (not shown) facilitating a bond between primary dressing 580 and first side 528 of second portion 534 of hinge member 526. Second portion 534 of hinge member 526 and adhesive layer 538 may extend beyond the perimeters of primary dressing 580. In this way, primary dressing 580 may be disposed on a patient's wound and secured in place by affixing hinge member 526 on the patient's skin adjacent to the wound on either side of the wound.

Primary dressing 580 may be formed from a variety of materials including foam, hydrogel, hydrocolloid, silicon, woven substrates, non-woven substrates or alginate. Depending on the application, primary dressing 580 may be hydrophobic or hydrophilic. Similarly, depending on the application, primary dressing 580 may be loaded with medicinal agents such as antimicrobial compounds, antifungal compounds and/or antibacterial compounds to reduce the risk of infection.

A protective member 540 may be releasably attached to hinge member 526 by adhesive layer 538. A release coating may be applied to the side of protective member 540, adjacent to adhesive layer 538 so that protective member 540 can be easily separated from hinge member 526 despite the presence of adhesive layer 538. Protective member 540 is at least coextensive with adhesive layer 538 so as to prevent undesired exposure of adhesive layer 538 prior to its application to a patient's skin. Provided that protective member 540 is at least co-extensive with adhesive layer 538, it may take any size, shape and configuration. Protective layer 540 may be advantageously fashioned to have dimensions different from those of handle member 512, so that protective member 540 can be readily removed from hinge member 526 when the device is to be applied to the patient's skin adjacent to the wound. Protective member 40 may be formed from a variety of materials, such as paper, polyester, polyethylene or laminates of these materials. Caregiver may sketch or write notes on protective member 40 and retain protective member 540 for future reference.

Figure 6:
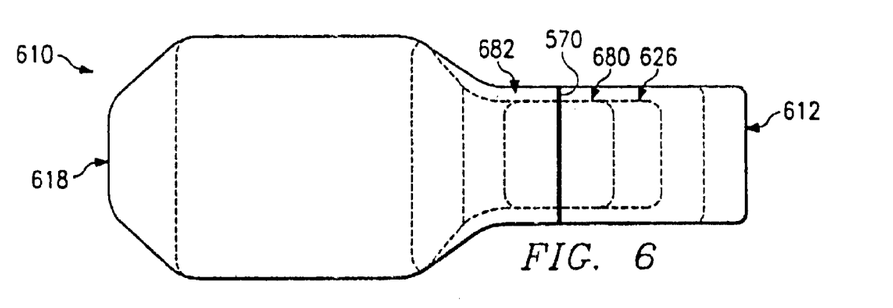
FIG. 6 is a schematic drawing showing a top view of a modified version of the wound covering device shown in FIG. 5A.

FIG. 6 shows a top view of another embodiment of a wound covering device 610 according to the teachings of the present invention. Although all the components are not shown in FIG. 6, the wound covering device 610 includes the same structural components as did the device 510 described in detail hereinbefore. The modification of FIG. 6, as compared to the wound covering device 510, resides in a change to the configuration of hinge member 526 and a primary dressing 680. While hinge member 526 and primary dressing 580 extend to meet the perimeter of handle member 512, the perimeters of hinge member 626 and primary dressing 680 have been excised, or kiss-cut, to form a dry edge 682 around a portion of the perimeters of hinge member 626 and primary dressing 680. Dry edge 682 protects against cold flow causing live adhesive to flow beyond the perimeters of handle member 512 and protective member 540. Because there is an adhesive layer between hinge member 626 and primary dressing 680, pressure applied to primary dressing 580 during shipping or handling may force the adhesive layer between the two to flow beyond the perimeters of these structures. The resulting live adhesive could cause difficulties if it were to contact packaging materials around wound covering device 610. Further, such live adhesive reduces an advantage of this invention; providing a wound covering device which is easy to apply, even when a caregiver is wearing Latex glove. By excising a portion of the perimeters of hinge member 626 and primary dressing 680, dry edge 682 may be formed. Dry edge 682 becomes a protective area, guarding against cold flow of adhesive from the perimeters of hinge member 626 and primary dressing 680.

Figure 7A:
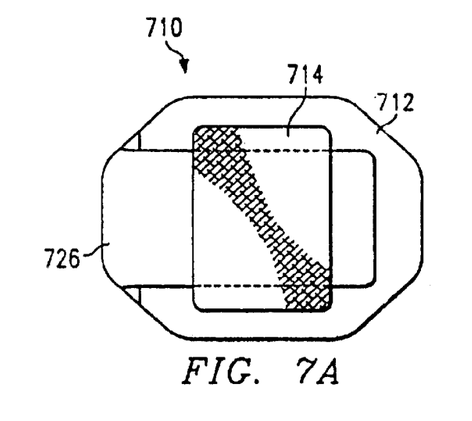
FIGS. 7A–7C are schematic drawings showing plan views of various embodiments of a wound covering device constructed according to teachings of the present invention.
Figure 7B:
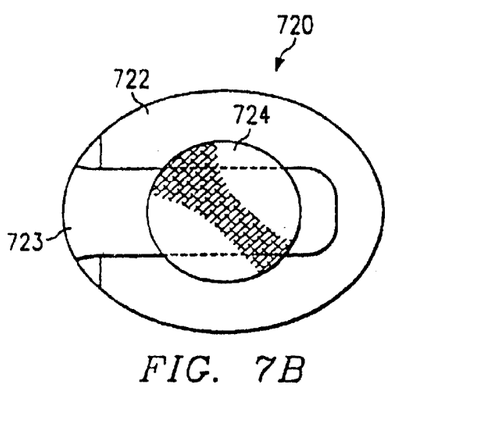
Figure 7C:
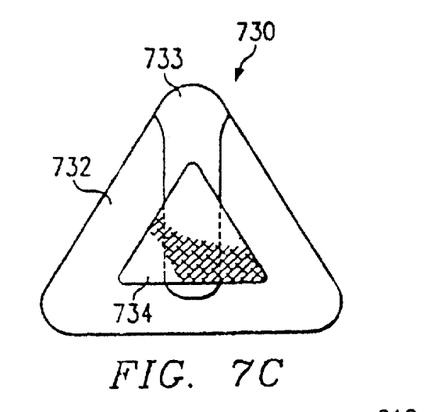

FIGS. 7A–7C illustrate various embodiments of wound covering devices according to teachings of the present invention. As shown, the hinge member, primary dressing and cover dressing may assume a variety of shapes, sizes and configurations depending on the application. The primary dressing may be any size relative to the hinge member. The cover dressing will generally be larger than the primary dressing to facilitate covering both the wound and the primary dressing and creating a seal around the portion of the wound to be covered.

FIG. 7A shows wound covering device 710 having hinge member 726, cover dressing 712 and primary dressing 714. Cover dressing 712 exhibits an octagonal shape and primary dressing 714 is rectangular. This configuration may be useful in a variety of applications. FIG. 7B shows a wound covering device 720 having a hinge member 723, an elliptical cover dressing 722 and a circular primary dressing 724. Wound covering device 720 may be advantageously applied to specific applications, such as covering pressure sores on a patient's hip, ankle, shoulder, elbow or heel. FIG. 7C illustrates a wound covering device 730 having hinge member 733, cover dressing 732 and primary dressing 734. Both cover dressing 732 and a primary dressing 734 exhibit a triangular shape. This configuration may be useful, for example, in an application to pressure sores in the sacral-coccyx area.

Figure 8:
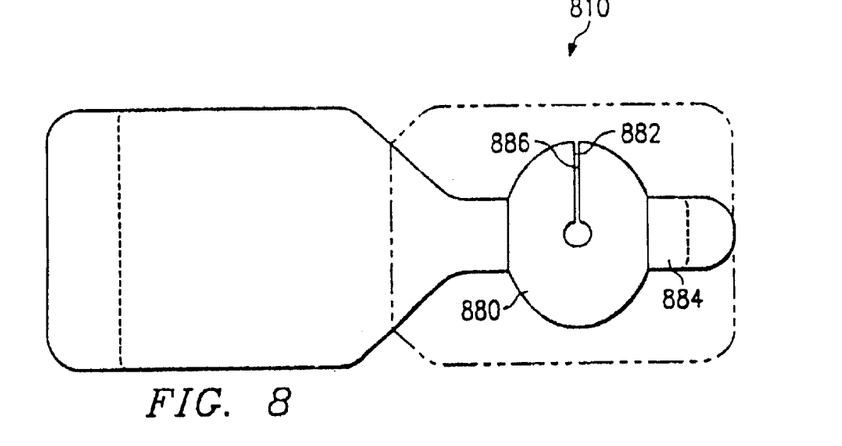
FIG. 8 is a schematic drawing showing a top view of still another embodiment of a wound covering device constructed according to teachings of the present invention.

FIG. 8 illustrates another embodiment of a wound covering device 810 in which a primary dressing 880 includes a first fenestration 882. Wound covering device 810 further includes a hinge member 884 having a second fenestration 886 corresponding to first fenestration 882 in primary dressing 880. Fenestration 882 and 886 facilitate placement of wound covering device 810 over a medical device such as a catheter or intravenous device extending from a patient's skin. In such applications, wound covering device 810 may serve to secure the medical device as well as to seal the skin around the medical device preventing moisture from escaping. Details of the application of wound covering device 810 to a medical device extending from a patient's skin are described below.

FIGS. 9A–9D show a method of applying a wound covering device according to the teachings of the present invention. A caregiver 5 begins the method of applying wound covering device 510 by removing wound covering device 510 from a sterile package (not shown). Upon removing wound covering device from its packaging, there is no live adhesive exposed. Caregiver 5 proceeds by grasping handle member 512 and cover dressing 518, and removing protective member 540 to expose adhesive layer 538 and primary dressing 580. Because there is no adhesive on the side of cover dressing 518 being grasped, wound covering device 510 will not stick to caregiver 5. Caregiver 5 may either dispose of protective member 540 or sketch or write notes on protective member 540 and retain it for future reference.

Figure 9A:
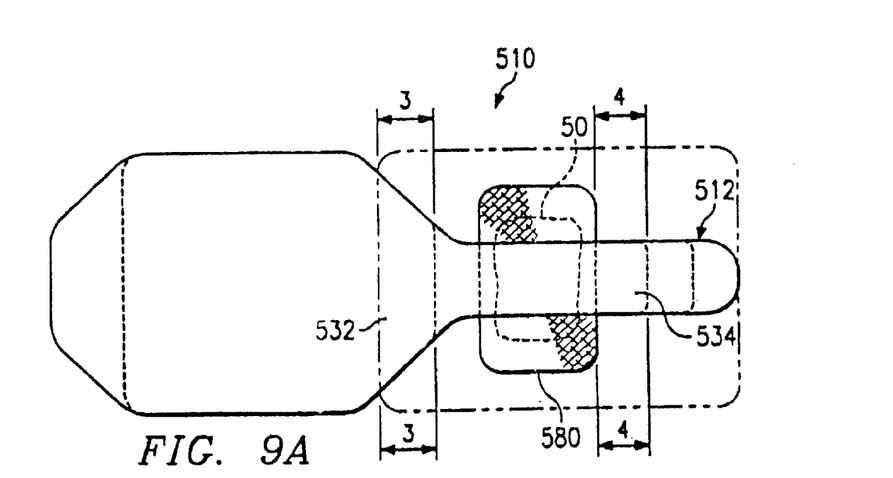
FIGS. 9A–9D are schematic drawings showing an exemplary method of applying a wound covering device according to teachings of the present invention.

If wound covering device 510 does not already include a primary dressing, caregiver 5 may affix primary dressing 580 to first side 528 of second portion 534 of hinge member 526. Caregiver 5 may next align primary dressing 580 over a wound 50 to be covered (FIG. 9A). If wound covering device 810 (FIG. 8) is used to cover and/or secure a medical device extending from a patient's skin, the caregiver will begin by aligning the medical device with fenestration 882 and 886 in primary dressing 880 and hinge member 884, respectively (FIG. 8). In that application, wound covering device 810 provides an advantage of enabling the caregiver to apply wound covering device 810 with one hand while holding the medical device secure with the other.

Once wound covering device 510 is properly aligned, caregiver 5 may apply pressure across area 3—3 to affix first portion 532 of hinge member 526 to a patient's skin 90 adjacent to the wound to be covered. Depending on the configuration of the wound covering device, caregiver 5 may or may not apply pressure over an area 4—4 to affix second portion 534 of hinge member 526 to an area of skin 95 adjacent to wound 50.

Figure 9B:
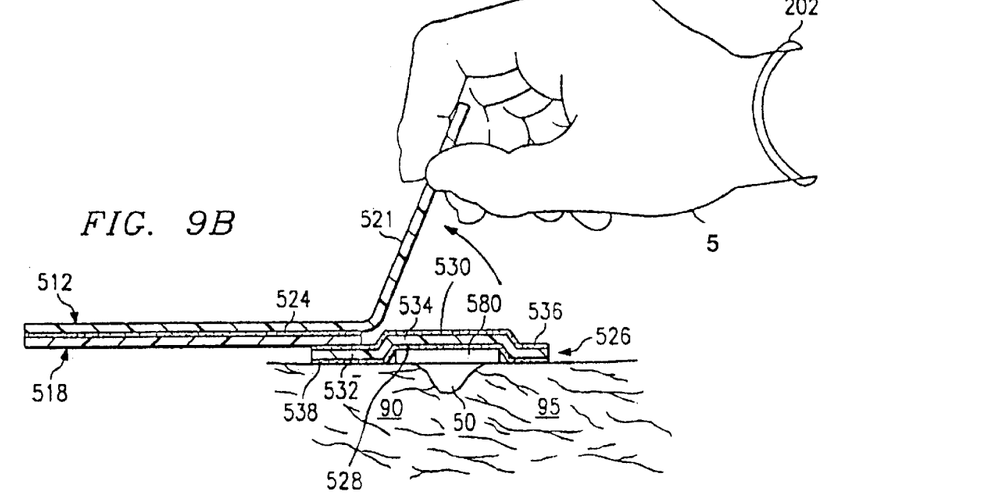
Figure 9C:
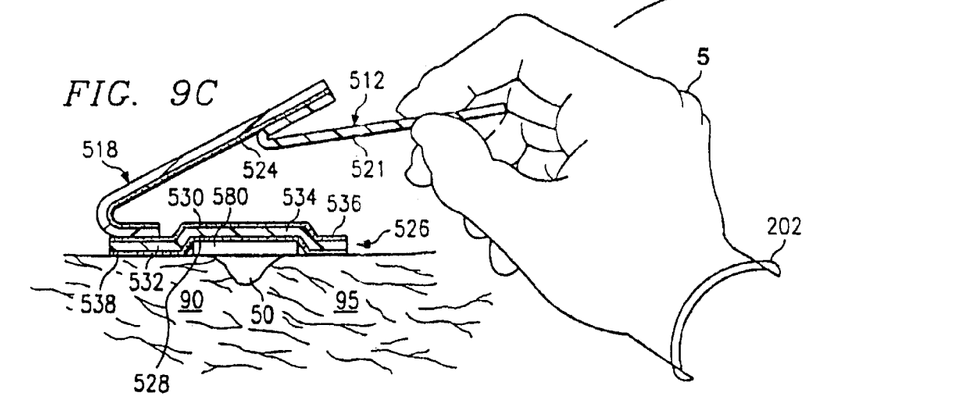
Figure 9D:
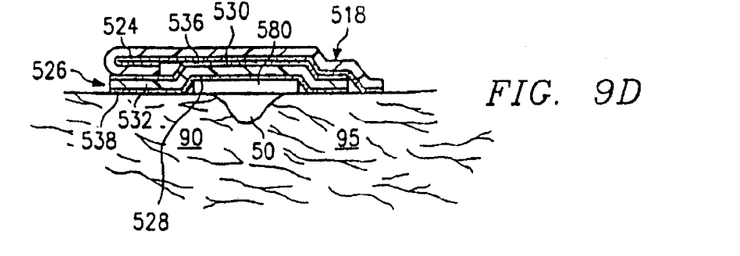

Once hinge member 26 has been affixed to the patient's skin adjacent to wound 50, caregiver 5 may grasp handle member 512 at an area remote from cover member 518, and peel handle member 512 away from hinge member 526 until cover dressing 518 is encountered (FIG. 9B). Upon encountering cover dressing 518, caregiver peels handle member 512 away from cover dressing 518, drawing cover dressing 518 over wound 50 and primary dressing 580 (FIG. 9C). Caregiver 5 continues to peel handle member 512 from cover dressing 518 until cover dressing 518 overlies primary dressing 580 and handle member 512 separates from cover dressing 518. Caregiver 5 may write notes or sketch on handle member 512, and retain handle member 512 in the patient's records for future reference. Once cover dressing 518 is disposed in an overlying relationship to primary dressing 580, caregiver 5 may apply pressure to cover member 518 to affix cover member 518 securely to the skin surrounding wound 50 (FIG. 9D). Cover member 518 forms a barrier around primary dressing 580 and wound 50. This barrier may prevent external contaminants from entering the wound site, and may also prevent wound exudates from leaking from the wound site.

ADDITIONAL DISCLOSURE

The following disclosure contains the specification and figures from application Ser. No. 08/278,575, U.S. Pat. No. 5,497,788. The present application is a continuation of the 08/858,015 application, which claims priority to the '575 application and incorporates the '575 application by reference in its entirety therein.

In accordance with the present invention, there is provided a unitary wound closure device adapted to permit a wound on a patient to be viewed while the closure device is secured to the patient. The device comprises a body having sufficient flexibility for it to be folded against itself. The body includes first and second surfaces facing away from one another, a securing portion having a length and width sufficient to secure facing edges of the wound in close juxtaposition with one another and a viewing portion having a length and width sufficient to circumscribe the wound on the patient. A first quantity of adhesive substance is disposed on the first surface of the body to adhere the securing portion of the body to the patient. A second quantity of adhesive substance is disposed on the second surface of the body to adhere the viewing portion to the patient and the securing portion when the viewing portion is folded over and onto the protecting portion and the patient.

Further, in accordance with the present invention, there is provided a method of protecting and viewing a wound in a patient that comprises positioning the edges of the wound in close juxtaposition relation to one another. A securing portion of a flexible material is then adhered to the patient with the edges of the wound in close juxtaposition. A viewing portion of the flexible material is folded over the securing portion of the flexible material. The viewing portion of the elongated flexible material is adhered to the patient and the securing portion of the flexible material to permit the wound to be viewed.

Turning now to FIGS. 10–40, there is shown a unitary wound closure device 100 adapted to permit a wound 120 on a patient 140 to be viewed while closure device 100 is secured to patient 140.

Figures 30, 40:
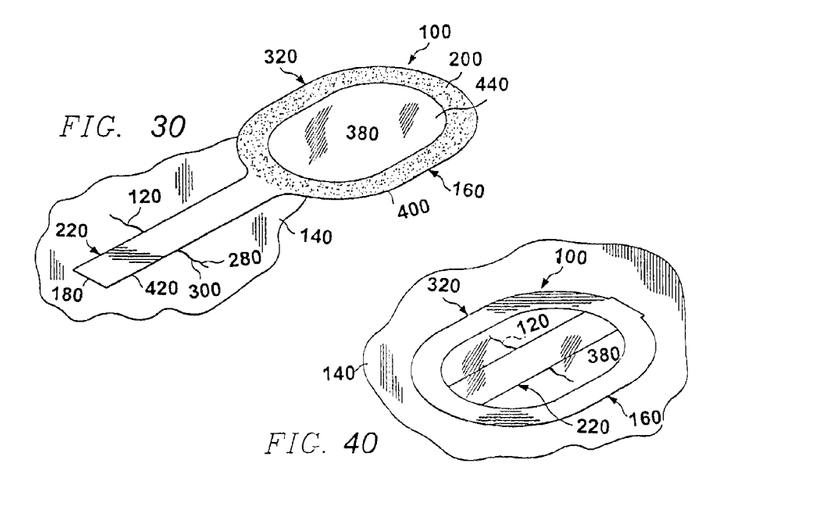
FIG. 30 is a perspective view of the device shown in FIG. 20 with a sheet of protective material removed from the device shown in FIG. 10.
FIG. 40 is a perspective view of the device shown in FIG. 30 with the viewing portion of the device secured to the patient and the securing portion of the device.

Device 100 comprises a body 160 having sufficient flexibility for it to be folded against itself, as best seen in FIG. 40.

Figures 10, 20:
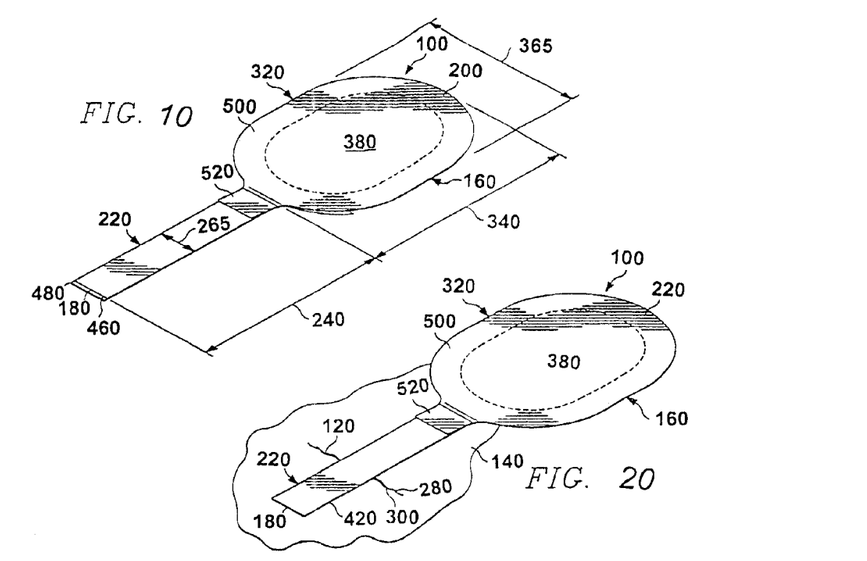
FIG. 10 is a perspective view of another embodiment of a device to close a wound on a patient constructed according to the present invention.
FIG. 20 is a perspective view of the device shown in FIG. 10 with the edges of the wound secured in close juxtaposition with one another and the securing portion of the device adhered to the patient.

Body 160 is made from a transparent plastic membrane and includes a first surface 180 and a second surface 200 facing away from surface 180.

As shown in FIGS. 20–40, a securing portion 220 is provided in body 160 and has a length 240 and a width 265 sufficient to secure facing edges 280 and 300 of wound 120 in close juxtaposition with one another. It has been found that when securing portion 220 has a width sufficiently small to permit viewing each side of the wound, wound closing device 10 works well by giving assurance to the viewer that he or she can see the ends of the wound 120.

A viewing portion 320 is provided in body 160 and has a length 340 and width 365 sufficient to circumscribe wound 120 on patient 140. To permit observation of wound 120 in patient 140 and securing portion 220 on body 160, a window 380 is provided and is circumscribed by a framing border 40.

Body 160, preferably, appears in the general shape of a miniature tennis racket. Viewing portion 320 is in the general configuration of an oval member to resemble the racket portion of the tennis racket and securing portion 220 is in the general configuration of an elongated member to resemble the handle portion of the tennis racket. The oval member permits bedding to be slipped over device 100 without snagging. The elongated member is of such size as to permit relatively easy viewing of edges 280 and 300 of wound 120 and of such strength as to retain edges 280 and 300 of wound 120 in close juxtaposition.

A first quantity of adhesive substance 420 is disposed on first surface 180 of body 160 to adhere securing portion 220 of body 160 to patient 140.

A second quantity of adhesive substance 440 is disposed on second surface 200 of body 160 and border 400 to adhere viewing portion 320 to patient 140 and further secure portion 220 when viewing portion 320 is folded over and onto securing portion 220 and patient 140.

A first sheet of protective material 460 covers a first quantity of adhesive substance 420. First sheet 460 has a width at least as wide as width 265 of securing portion 220 and a length longer than length 240 to provide a lip 480, which extends beyond first quantity of adhesive substance 420 by a distance sufficient to allow lip 480 to be gripped by a finger and thumb encased within a rubber glove.

A second sheet of protective material 500 covers a second quantity of adhesive substance 440. Second sheet 500 has a width at least as wide as width 365 of viewing portion 320 and a length longer than length 340 to provide a lip 520, which extends beyond second quantity of adhesive substance 440 by a distance sufficient to allow lip 520 to be gripped by a finger and thumb encased within a rubber glove.

It has been found desirable to increase the stability of viewing portion 320 after second sheet 480 is removed from membrane of body 160 by making the border from a relatively inflexible material that is sufficiently inflexible to provide the desired stiffness while be sufficiently flexible to conform to the contours of patient 140, such as spun bonded Nylon.

In operation, a health care provider positions patient 140 with wound 120 at a convenient position to secure edges 280 and 300 together. While edges 280 and 300 are positioned close to one another, lip 480 of first protective sheet 460 is grasped between a finger and thumb encased within a rubber glove of the health care provided and protective sheet 460 is removed from securing portion 220. Securing portion 220 is then secured on patient 140 as shown in FIG. 20 so that edges 280 and 300 are secured in close juxtaposition with one another. Then, as shown in FIG. 30, lip 520 of second protective sheet 500 is grasped between a finger and thumb encased within a rubber glove of the health care provider and protective sheet 500 removed from viewing portion 320. Viewing portion 320 is then folded over securing portion 220 and secured to securing portion 220 and patient 140, as shown in FIG. 40. After being secured to patient 140, the health care provider can see wound 120 to determine the status of the healing process or whether infection is developing.

Although the present invention and its advantages have been described in detail, it should be understood that various changes, substitutions, and alterations can be made therein without departing from the spirit and scope of the invention as defined in the following claims.

What is claimed:

1. A wound closure device for treating a wound on a patient, comprising:
   a body having sufficient flexibility so as to be folded against itself, said body comprising first and second surfaces facing away from each other, a securing portion configured to be adhered to a patient's skin at least in an area adjacent the wound, and a viewing portion having a length and width sufficient to circumscribe the wound on the patient;

said first surface forming an integral part of said securing portion;

a first quantity of adhesive substance disposed on said first surface of said body for adhering said securing portion to the patient; and said second surface of said viewing portion configured to cover the wound and be secured to the patient's skin when said viewing portion is folded over the wound and pressed onto the patient's skin.

2. The wound closure device as in claim 1, wherein said securing portion comprises a width and length sufficient to extend across the wound, said viewing portion also covering at least a portion of said securing portion when folded over the wound.

3. The wound closure device as in claim 2, wherein the wound is of a type defined by separated facing edges in the patient's skin, said securing portion securing the facing edges of the wound in close juxtaposition.

4. The wound closure device as in claim 2, wherein said viewing portion formed of a substantially transparent material for viewing the wound and securing portion.

5. The wound closure device as in claim 2, further comprising an additional quantity of adhesive disposed on said second surface of said securing portion for adhering said viewing portion to said securing portion when said viewing portion is folded over the wound.

6. The wound closure device as in claim 5, further comprising an additional quantity of adhesive disposed on said second surface of said viewing portion for adhering said viewing portion to the patient's skin when said viewing portion is folded over the wound.

7. The wound closure device as in claim 1, further comprising an additional quantity of adhesive disposed on said second surface of said viewing portion for adhering said viewing portion to the patient's skin when folded over the wound.

8. The wound closure device as in claim 1, further comprising an additional quantity of adhesive disposed on said second surface of said securing device for adhering said viewing portion to at least at a portion of said securing portion.

9. The wound closure device as in claim 1, wherein said viewing portion is formed from a substantially transparent material through which the wound on the patient may be viewed.

10. The wound closure device as in claim 1, further comprising:

a hinge member attached at one end thereof to said viewing portion and having a first side with an adhesive thereon for securing said first side to the patient's skin at least in an area adjacent the wound, said first side facing opposite from said second surface of said viewing portion, said hinge member having a second side releasably attached to said securing portion on the same side thereof as said second surface of said viewing portion; and wherein once said first side of said hinge member is pressed against a patient's skin adjacent to the wound, said securing portion is used to pull and fold said viewing portion over said hinge member to press said second surface thereof to the patient's skin whereby said viewing portion covers the wound and is held against the skin surrounding the wound.

11. The wound closure device as in claim 10, wherein said first side of said hinge member has a length so as to be adhered to the patient's skin adjacent to but not to extend over the wound.

12. The wound closure device as in claim 10, wherein said first side of said hinge member has a length so as to be adhered to the patient's skin adjacent to the wound and to extend over the wound, said viewing portion thereby covering the wound and at least a portion of said hinge member extending over the wound.

13. The wound covering device as in claim 10, wherein said hinge member comprises a medicinal agent for assisting in healing the wound.

* * * * *